(12) United States Patent
Glukhovsky et al.

(10) Patent No.: US 8,216,130 B2
(45) Date of Patent: Jul. 10, 2012

(54) DEVICE, SYSTEM AND METHOD FOR SELECTIVE ACTIVATION OF IN VIVO SENSORS

(75) Inventors: Arkady Glukhovsky, Santa Clarita, CA (US); Mordechsi Frisch, Moreshet (IL); Tal Davidson, Yoqneam Illit (IL); Gavriel Meron, Petach Tikva (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 12/854,483

(22) Filed: Aug. 11, 2010

(65) Prior Publication Data

US 2010/0324381 A1 Dec. 23, 2010

Related U.S. Application Data

(63) Continuation of application No. 10/493,751, filed as application No. PCT/IL03/01080 on Dec. 16, 2003, now abandoned.

(60) Provisional application No. 60/433,586, filed on Dec. 16, 2002.

(51) Int. Cl.
*A61B 1/04* (2006.01)

(52) U.S. Cl. ........ 600/118; 600/109; 600/160; 600/476; 600/477

(58) Field of Classification Search .................. 600/407, 600/476, 477, 160, 118, 109–113; 345/45, 345/46, 49, 65, 68, 70
See application file for complete search history.

(56) References Cited

U.S. PATENT DOCUMENTS

| | | | |
|---|---|---|---|
| 3,723,644 A | 3/1973 | Haskell et al. | |
| 4,631,582 A | 12/1986 | Nagasaki et al. | |
| 5,585,840 A | 12/1996 | Watanabe et al. | |
| 5,604,531 A | 2/1997 | Iddan et al. | |
| 5,749,830 A | 5/1998 | Kaneko et al. | |
| 5,833,603 A * | 11/1998 | Kovacs et al. | 600/317 |
| 6,219,091 B1 | 4/2001 | Yamanaka et al. | |
| 6,240,312 B1 | 5/2001 | Alfano et al. | |
| 6,254,531 B1 | 7/2001 | Higuchi et al. | |
| 6,364,829 B1 | 4/2002 | Fulghum | |

(Continued)

FOREIGN PATENT DOCUMENTS

JP 62-019857 1/1980

(Continued)

OTHER PUBLICATIONS

Office Action, issued Apr. 13, 2010, for U.S. Appl. No. 10/551,053.

(Continued)

*Primary Examiner* — Brian Casler
*Assistant Examiner* — Amanda Lauritzen
(74) *Attorney, Agent, or Firm* — Pearl Cohen Zedek Latzer, LLP

(57) ABSTRACT

A device, system and method for selectively activating or altering the operational mode of an autonomous in vivo device in response to in vivo conditions. They system may include an in vivo sensing device with a condition tester, and a controller. The in vivo sensing device may be in communications with an external receiver. The condition tester may include at least one layer of a dissolvable material coated on at least a portion of the autonomous device. The layer may dissolve when exposed to a specific material of a specified site along the GI tract. A sensor may be exposed when the layer dissolves or a switch autonomously activated with the layer dissolves.

20 Claims, 9 Drawing Sheets

U.S. PATENT DOCUMENTS

| | | | |
|---|---|---|---|
| 6,462,770 | B1 | 10/2002 | Cline et al. |
| 6,635,834 | B1 * | 10/2003 | Wenner ............... 200/61.08 |
| 6,667,765 | B1 | 12/2003 | Tanaka |
| 6,939,292 | B2 | 9/2005 | Mizuno et al. |
| 7,022,067 | B2 | 4/2006 | Glukhovsky et al. |
| 7,083,578 | B2 * | 8/2006 | Lewkowicz et al. ........ 600/593 |
| 7,112,752 | B1 * | 9/2006 | Wenner ............... 200/61.04 |
| 7,160,258 | B2 * | 1/2007 | Imran et al. ............... 600/593 |
| 7,214,182 | B2 | 5/2007 | Shimizu et al. |
| 7,251,383 | B2 * | 7/2007 | Iddan ........................ 385/12 |
| 7,355,625 | B1 | 4/2008 | Mochida et al. |
| 7,419,468 | B2 | 9/2008 | Shimizu et al. |
| 7,511,733 | B2 | 3/2009 | Takizawa |
| 7,724,928 | B2 | 5/2010 | Glukhovsky |
| 7,970,455 | B2 * | 6/2011 | Zilberstein et al. ........ 600/436 |
| 2002/0099310 | A1 | 7/2002 | Kimchy et al. |
| 2002/0103417 | A1 | 8/2002 | Gazdzinski |
| 2002/0132226 | A1 * | 9/2002 | Nair et al. ..................... 435/4 |
| 2003/0077223 | A1 | 4/2003 | Glukhovsky et al. |
| 2004/0073087 | A1 | 4/2004 | Glukhovsky et al. |
| 2004/0138558 | A1 | 7/2004 | Dunki-Jacobs et al. |
| 2004/0162501 | A1 | 8/2004 | Imran |
| 2004/0180391 | A1 * | 9/2004 | Gratzl et al. ................ 435/14 |
| 2004/0210105 | A1 | 10/2004 | Hale et al. |
| 2005/0110881 | A1 | 5/2005 | Glukhovsky et al. |
| 2005/0183733 | A1 | 8/2005 | Kawano et al. |
| 2007/0225560 | A1 | 9/2007 | Avni |
| 2008/0269664 | A1 * | 10/2008 | Trovato et al. ............. 604/20 |
| 2009/0306632 | A1 * | 12/2009 | Trovato et al. .......... 604/890.1 |

FOREIGN PATENT DOCUMENTS

| | | |
|---|---|---|
| JP | 01-305925 | 12/1989 |
| JP | 04-138128 | 5/1992 |
| JP | 07-111985 | 5/1995 |
| JP | 08-503384 | 4/1996 |
| JP | 2002/508201 | 3/2002 |
| JP | 2002-186672 | 7/2002 |
| JP | 2003-038424 | 2/2003 |
| WO | WO 94/01165 | 1/1994 |
| WO | WO 02/058531 | 8/2002 |
| WO | WO 02/095351 | 11/2002 |
| WO | WO 2004/082472 | 9/2004 |

OTHER PUBLICATIONS

Final Office Action, issued Sep. 28, 2010, for U.S. Appl. No. 10/551,053.

Office Action issued Feb. 19, 2009 for U.S. Appl. No. 11,1267,173.

Office Action issued Sep. 8, 2009 for U.S. Appl. No. 11/267,173.

Office Action issued Jun. 4, 2009 for U.S. Appl. No. 10/551,053.

Office Action issued Dec. 23, 2009 for U.S. Appl. No. 10/551,053.

Office Action issued for U.S. Appl. No. 11/794,539 and dated Oct. 3, 2011.

Office Action, issued Apr. 13, 2010, for U.S. Appl. No. 11/267,173.

Office Action, issued Aug. 23, 2010, for U.S. Appl. No. 11/267,173.

* cited by examiner

DEVICE, SYSTEM AND METHOD FOR SELECTIVE ACTIVATION OF IN VIVO SENSORS

CROSS-REFERENCE TO RELATED APPLICATIONS

The present application is a continuation of U.S. Nonprovisional application Ser. No. 10/493,751, filed Apr. 27, 2004, now abandoned entitled "DEVICE, SYSTEM AND METHOD FOR SELECTIVE ACTIVATION OF IN VIVO SENSORS", which is a National Phase Application of PCT International Application No. PCT/IL03/01080, filed Dec. 16, 2003, entitled "DEVICE, SYSTEM AND METHOD FOR SELECTIVE ACTIVATION OF IN VIVO SENSORS", which in turn claims the priority of U.S. Provisional Application Ser. No. 60/433,586, filed on Dec. 16, 2002, entitled "DEVICE, SYSTEM AND METHOD FOR SELECTIVE ACTIVATION OF IN VIVO SENSORS", all of which are incorporated herein by reference in their entirety.

FIELD OF THE INVENTION

The present invention relates to the field of in vivo devices. More specifically, the present invention relates to a device, system and method for selectively activating or altering the operational mode of an in vivo device, for example, in response to in vivo conditions.

BACKGROUND OF THE INVENTION

Certain in vivo devices may be introduced into a body in a location remote to the area where their sensing, diagnosing or other functions may be performed. For example, an in vivo device for imaging areas of the small intestine may be introduced into a body through the mouth and pass through the stomach and other parts of the gastrointestinal (GI) tract by way of peristalsis until reaching the small intestine. Similarly, an in vivo device may be introduced into a body wherein the location of an area of interest or of a suspected pathology may be unknown or uncertain, thereby necessitating that an in vivo device pass from its point of introduction and locate the area of pathology where its sensing functions or other functions may be required for diagnosing pathologies or performing other functions.

In vivo devices such as sensors are generally configured to capture sensory data on a fixed schedule that may be set or programmed into the in vivo sensor before it may be introduced into a body. For example, an in vivo image sensor may be configured to capture images at fixed intervals beginning with the time that it is introduced into the body. Typically, an in vivo sensor may be activated by a doctor or medical practitioner who assists in introducing such sensor into the body. Other in vivo sensors may be activated before ingestion, for example, automatically upon their removal from their original packaging. As a result, an in vivo sensor introduced to a location in the body that may be remote from an area of interest or suspected pathology in a body, may perform its sensing functions or other functions in locations other than the area of interests for example where no pathology or suspected pathology exists. The performance of such superfluous sensing may inefficiently utilize the power supply, data collection, data transfer (bandwidth), data storage capacity and/or other of the sometimes limited resource of the in vivo sensor. Redundant data may be required to be reviewed by the physician, increasing the overall review time.

The capturing of data by an in vivo sensor based on a fixed schedule may result on the one hand, in superfluous data being collected in areas that may be of little diagnostic or other interest, and, on the other hand, in insufficient sensory data being captured of in vivo areas that may be of particular diagnostic or other interest. For example, an in vivo image capturing system may be programmed to capture in vivo images at a rate of, for example, two frames per second. While such frame capture rate may be for example sufficient to generally capture adequate images of most of the small bowel, such frame capture rate may be too slow to achieve the level of imaging detail that may be required for areas such as the esophagus or other areas.

There is therefore a need for a system and method for allowing an efficient and effective operation of an in vivo device.

SUMMARY OF THE INVENTION

There is thus provided according to one embodiment of the invention, a system for in vivo sensing including for example an in vivo sensing device with a condition tester, and a controller. The condition sensor may for example be operatively linked with the controller so as to control for example an operational mode of the in vivo sensing device.

It is also provided according to an embodiment of the invention, a method for controlling, for example an in vivo imaging device by, for example, sensing a condition in vivo and triggering an event in the in vivo imaging device based on the sensing.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

Figure 1A:
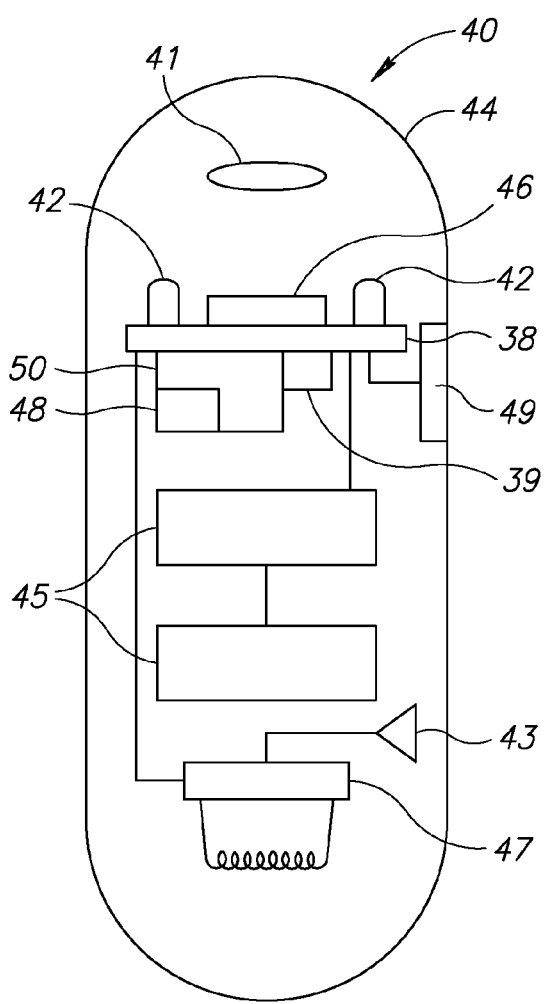
FIG. 1A is a schematic illustration of an in vivo device that may be used in accordance with an embodiment of the present invention.

In the following description, various aspects of the present invention will be described. For purposes of explanation, specific configurations and details are set forth in order to provide a thorough understanding of the present invention. However, it will also be appreciated by one skilled in the art that the present invention may be practiced without the specific details presented herein. Furthermore, well-known features may be omitted or simplified in order not to obscure the present invention.

According to some embodiments of the invention, a system, method and device are provided for triggering an event such as, for example, activating or altering the operational mode of an in vivo device and/or a receiving (and/or processing, and/or reviewing) unit, typically located outside a patient's body, in response to in vivo conditions as may be detected by an in vivo condition tester. Such activating, deactivating or altering operational modes may include for example, activating or deactivating one or more components of the in vivo device and/or the receiving unit, increasing or decreasing the power consumption, increasing or decreasing the level of illumination, increasing or decreasing the rate of sensing, such as, for example, increasing the data capture rate from, for example, 2 images per second to for example, 14 images per second, or altering the sensing parameters such as, for example, in the case of an in vivo image sensor, increasing or decreasing the illumination intensity of the light sources or altering the image plane of the image sensor. Other operational modes may be changed and other data capture rates may be used. In certain embodiments, more than one in vivo sensor may be included in a single device. A change in the operational mode of the device may in such embodiments include activating or deactivating one or both of such sensors or alternating the activation of such more than one sensor. For example, an in vivo image sensor may include two image sensors. A change in operational mode may in such example mean activating or deactivating one or both of such image sensors, or alternating the activation of such image sensors. In other embodiments, one in vivo device may activate or deactivate one or more components in second in vivo device. Communication between two or more in vivo devices may be for example through one or more external receivers or may be through for example direct communication between one or more in vivo devices.

In certain embodiments changes in the operational mode may for example include changes in the methods or procedures of processing sensory data obtained, and optionally transmitted, from the in vivo device. For example, sensory data such as images or ultrasound readings from endo-luminal areas that have villi may return distorted images as a result of the irregular surfaces of the villi. In certain cases, such distortions may be corrected through changes in the methods of processing of the sensory data by the data processor. For example, specific image processing algorithms may be activated. According to one embodiment methods of processing sensory data may be executed, for example, in an external receiving unit. In another embodiment the change may be in the mode of the data presentation (reviewing mode), e.g. presentation of the images in double image vs. single image mode.

The invention according to certain embodiments, comprises an in vivo device such as, for example, an in vivo image capture system, an in vivo condition tester such as, for example, any of an in vivo pH tester, blood detector, thermometer, pressure tester, spectral analytic image sensor, biosensor for biosensing, accelerometer, or motion detector, and a controller for linking the condition tester with the in vivo device and for signaling the change to be made in the operational mode of the in vivo device. Other condition testers may also be used as well as a combination of two or more condition sensor may be used. In one exemplary embodiment a biosensor may be used to sense, for example, colon specific flora in a colon. In another exemplary embodiment a pressure tester may be used to sense, for example, a change in pressure, such as a change in pressure pattern. For example, a drop in pressure may be sensed by a pressure tester, for example, when the device moves from the small intestine to the cecum (at the beginning of the colon). Various signals emitted by the condition tester such as mechanical, electrical, electromagnetic, chemical, or optical signals may also be used.

Embodiments of the present invention may be used with in vivo devices and recording/receiving and display systems such as various embodiments described in U.S. Pat. No. 5,604,531, assigned to the common assignee of the present application and incorporated herein by reference, and/or Publication Number WO 01/65995, also assigned to the common assignee of the present application and incorporated herein by reference. Other in vivo systems, having other configurations, may be used.

Embodiments of the device may be typically autonomous and typically self-contained. For example, the device may be a capsule or other units where all the components are substantially contained within a container or shell, and where the device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

An in vivo imaging system for example, that may be included in an ingestible device such as a capsule may capture and transmit images of the GI tract while the capsule is may pass through the GI lumen. In addition to the imaging system, a device such as a capsule may include, for example, an optical system for imaging an area of interest onto the imaging system and a transmitter for transmitting the image output of the image sensor. A capsule may pass through the digestive tract and operate as an autonomous video endoscope. It may image difficult to reach areas of the GI tract, such as the small intestine. Other devices may be included, and devices including sensors other than image sensors may be used. Configurations other than capsules may also be used.

Reference is made to FIG. 1A, a schematic illustration of an in vivo device in the form of for example, a swallowable capsule that may be used in accordance with an embodiment of the present invention. Device 40 may comprise an image sensor 46, an in vivo optical system 41 for focusing light reflected back from in vivo areas (not shown) onto image sensor 46, an illumination source 42, such as one or more light emitting diodes (LEDs) or other suitable sources, a dome 44 that may be useful, inter alia, for protecting the optical system from body fluids, a circuit or controller 48 for controlling the operational mode, such as for example settings of the device 40, a condition tester 49 such as for example, a pH tester or thermometer, an in vivo memory unit 39, an in vivo power source 45 such as a set of batteries, an in vivo receiver 43 for collecting signals transmitted to device 40, and an in vivo transmitter 47 for transmitting signals and/or image data to a receiver. One or more of in vivo image sensor 46, in vivo illumination source 42, controller 48, in vivo memory unit 39, in vivo transmitter 47, in vivo receiver 43 and condition tester 49 may in certain embodiments of the present invention be operatively connected, for example to/or through PCB 38, or included or embedded within an application specific integrated circuit (ASIC) 50. In other embodiments, image sensor 46, controller 48 and condition tester 49 may be operatively linked to each other without an ASIC 50 or PCB 38 or other connecting means. A wired or wireless connection, such as for example a microwave connection or other suitable connections may be used between elements in the capsule. Such an ASIC 50 may provide control for the capsule. Alternatively, another component such as transmitter 47 may provide such control.

In certain embodiments, image sensor 46 may be a CCD or a CMOS image sensor that may have arrays of various typically color pixels. Other suitable image sensors or no image sensors may be used. In one embodiment of the invention, image sensor 46 may also function as a condition tester. For example, an image sensor may be used to detect for example, blood vessel structures typically found in colon, or villi structures typically found in small intestine. Detection of such structures, detection of lack of such structures, or detection of other structures or colors such as for example color specific to content in the intestine may be used to trigger an event in the in vivo device. Other suitable structures or colors detected may be used as a trigger. Detection, according to an embodiment of the invention, could be aided by appropriate image processing algorithms and/or suitable software.

In other configurations of device 40, components such as capsule receiver 43, power source 45, in vivo memory unit 39 or other units may be omitted.

Typically, device 40 is swallowed by a patient and traverses a patient's GI tract. Other suitable body lumens or cavities may be imaged or examined.

Figure 1B:
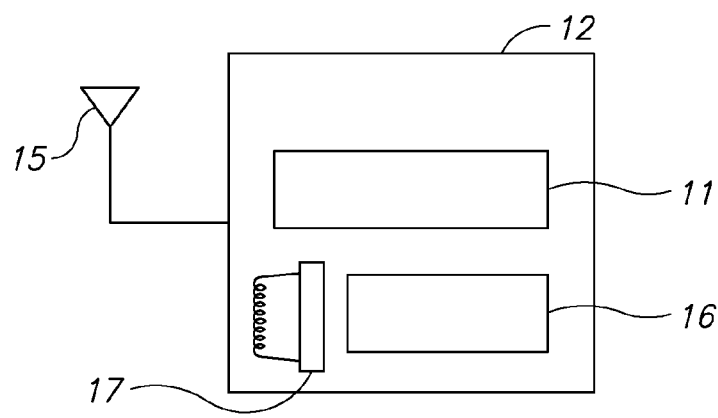
FIG. 1B is a schematic illustration of a receiver in accordance with an embodiment of the present invention.

Reference is now made to FIG. 1B, a schematic illustration of an external receiver 12 in accordance with an embodiment of the present invention. External receiver 12 may typically be located outside the patient's body and may receive and/or record and/or process the data transmitted from device 40. External receiver 12 may typically include a receiver antenna (or antenna array) 15, for receiving image and other data from device 40 and stored in for example storage unit 16. Typically, external receiver 12 may be portable, and may be worn on the patient's body during recording of the images.

External receiver 12 may also be equipped with processing unit 11, such as for example signal processing unit and/or control software or for example a control mechanism or circuit emulating such functionality that may control for example, evaluate and respond to signals transmitted by device 40. External receiver 12 may also include a transmitter and receiver transmitter 17 that may enable external receiver 12 to transmit signals such as control signals to device 40. External receiver 12 may also include a user interface (not shown) that may inter alia provide indications to a user or patient as to changes made in the operational mode of a device. For example, passage of a capsule through the stomach may be identified by changes detected in pH levels that may for example trigger a change in the operational mode of a sensor such as an image sensor. A patient may be signaled via a user interface that such mode change is being made and prompted to take certain actions such as for example, changing positions (such as for example, changing from a sitting position to a reclining position), ingesting a laxative, or certain liquids, etc.

Figure 1C:
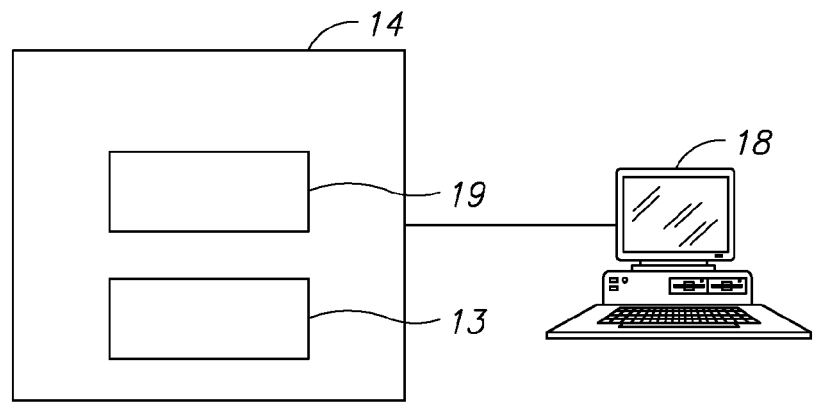
FIG. 1C is a schematic illustration of a data processor in accordance with an embodiment of the present invention.

Reference is now made to FIG. 1C, a schematic illustration of a data processor in accordance with an embodiment of the present invention. Preferably, data processor 14, data processor storage unit 19 and monitor 18 are part of a personal computer or workstation that may include standard components such as a processor 13, a memory (such as storage unit 19, or other memory), a disk drive, and input-output devices. Alternate configurations are possible. In alternate embodiments, the data reception and storage components may be of another configuration. Further, image and other data may be received in other manners, by other sets of components. Typically, in operation, image data is transferred from external receiver 12 to data processor 14, which, in conjunction with processor 13, storage 19, and software, stores, possibly processes, and displays the image data on monitor 18. Other systems and methods of storing and/or displaying collected image data may be used. In other embodiments, processing of data can be performed by components within the external receiver 12.

Typically, device 40 may capture an image and transmit the image by using, for example, radio frequencies, to receiver antenna(s) 15. In alternate embodiments external receiver 12 is an integral part of data processor 14. Typically, the image data recorded and transmitted is digital color image data, although in alternate embodiments other suitable image formats (e.g., black and white image data, infrared image data, etc.) may be used. In one embodiment, each frame of image data may include 256 rows of 256 pixels each, each pixel including data for color and brightness, according to known methods. For example, color may be represented in each pixel by a mosaic of four sub-pixels, each sub-pixel corresponding to primaries such as red, green, or blue (where one primary is represented twice). The brightness of each sub-pixel may be recorded by, for example, a one byte (i.e., 0-255) brightness value. Other data suitable formats may be used. In one embodiment, image sensor 46 may capture or transmitter 47 may transmit image or other data in a diluted mode, capturing or transmitting for example, 16 rows of 16 pixels each.

In an embodiment, in vivo transmitter 47 may include at least a modulator (not shown) for modulating the image signal from the image sensor 46, a radio frequency (RF) amplifier (not shown), and an impedance matcher (not shown). The modulator may convert the input image signal that may have for example, a cutoff frequency $f_c$ of less than 5 MHz to an RF signal having a carrier frequency $f_r$, that may typically be in the range of 1 GHz. The carrier frequency may be in other bands, e.g. a 400 MHz band. The modulated RF signal may typically have an appropriate bandwidth of $f_r$. The impedance matcher may match the impedance of the circuit to that of the antenna. Other suitable transmitters or arrangements of transmitter components may be used, utilizing different signal formats and frequency ranges. In one embodiment of device 40, transmission may occur at a frequency for example of 434 MHz, using for example Phase Shift Keying (PSK) or MSK (Minimal Shift Keying). In alternate embodiments, other suitable transmission frequencies and methods, such as for example AM or FM may be used.

External receiver 12 may detect a signal having the carrier frequency $f_r$, and the bandwidth $f_c$ such as described hereinabove. External receiver 12 may be similar to those found in televisions or it may be one similar to those described on pages 244-245 of the book "Biomedical Telemetry" by R. Stewart McKay and published by John Wiley and Sons, 1970. The receiver may be digital or analog. In alternate embodiments, other receivers, responding to other types of signals, may be used.

In certain embodiments, condition tester 49 may be an in vivo pH tester, as is well known in the art, for example a pH tester using the technology used in known pH measuring capsules. Such pH tester may utilize as electrodes an external ring electrode made of antimony and the zinc-silver chloride electrode of the battery that powers the tester. A saline solution such as for example, a 0.9% physiologic saline solution may be introduced into the electrode chamber immediately prior to the testing. The potential difference that develops between the two electrodes and that depends on the pH may be applied to a transistor as a frequency-determining measuring voltage.

Other pH testers, such as ion selective field effect transistors (ISFET), may also be used as condition tester 49 to evaluate pH in areas adjacent to the location of the device 40. ISFET sensor chips that may be used for in vivo pH detection are known in the art as may be described, for example, in Wang, L., Integrated Micro-Instrumentation for Dynamic Monitoring of the Gastro-Intestinal Tract, as presented at the IEEE Instrumentation and Measurement Technology Conference, May 2002, retrieved on Oct. 15, 2002 from the Internet: <URL: http://www.see.ac.uk/naa.publications.html>. Other suitable pH testers may also be used. An ISFET sensor serving as condition tester 49 may be operatively connected to ASIC 50 or otherwise may be connected directly to image sensor 46. In a typical embodiment, an ISFET sensor serving as condition tester 49 may be situated adjacent to the outer wall of the device 40 so as to maximize the exposure of such condition tester 49 to the in vivo conditions outside of such wall of device 40.

In some embodiments, controller 48 may be substituted or complimented by an external controller located out of the body. For example the external controller may be an integral part of processor 11. In such embodiments, triggering may be external triggering. Condition tester 49 may transmit a signal to in vivo transmitter 47 that transmits such signals to receiver antenna(s) 15. External receiver 12 may process such signals and transmit back triggering signal such as instructions by way of receiver transmitter 17 to in vivo receiver 43. In vivo receiver 43 may then direct a change in the mode of operation of device 40. In some embodiments, external receiver 12 may be capable of overriding or initiating a change in the mode of operation of device 40 in response to a signal that is input to receiver by medical personnel.

A condition tester such as for example, a pressure sensor may use a strain gauge as a condition detector, such as for example, a thin foil, typically a semiconductor or a piezoelectric material. Such strain gauge may accept power through a wire and provide a variable strain signal on such wire.

Figure 2:
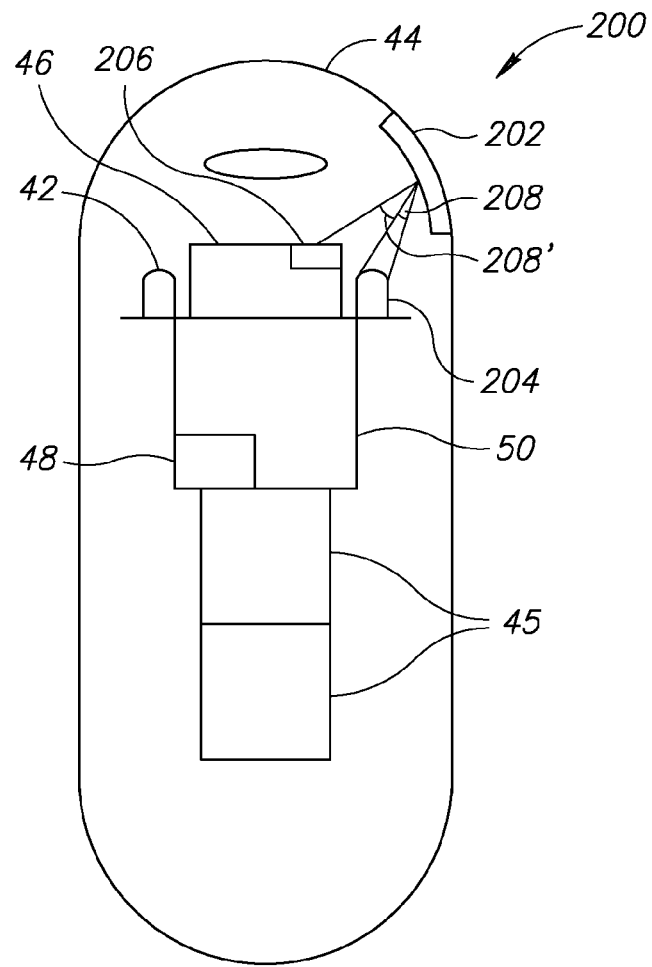
FIG. 2 is a schematic illustration of an in vivo device with a condition sensitive, color-changing material in accordance with an embodiment of the present invention.

In other embodiments, condition tester 49 may take the form of a condition sensitive, color-changing material. Reference is now made to FIG. 2, which is a schematic illustration of an in vivo sensor with a condition sensitive, color-changing material 202 in accordance with an embodiment of the present invention. Material 202 may be temperature sensitive. "Temperature-sensitive" in the context of the present invention may be defined as reactive to a change in temperature. This temperature change may include a range of temperatures or a change from a reference temperature to another temperature. In other embodiments, material 202 may be pressure-sensitive, pH sensitive or sensitive to the presence of certain substances such as for example, blood, with color-changing characteristics varying with changes in such conditions. Thus, different properties within the environment of the body lumen can be measured in a manner similar to the one described for temperature hereinbelow. For example, a pH condition tester may use litmus paper as a color-changing material 202, and a blood detector may use a polyelectrolyte as a color-changing material 202, as known in the art.

In an embodiment, the temperature-sensitive, color-changing material 202 may be a Thermotropic Liquid Crystal (TLC) paint or coating, such as are offered by Hallcrest, Inc. of Glenview, Ill. The TLCs, that may, for example, be cholesteric (including sterol-derived chemicals) or chiral nematic (including non-sterol based chemicals) liquid crystals, or a combination of the two, provide color changes in response to temperature changes. These color changes may be reversible or hysteretic. In certain embodiments that include materials 202 that may be capable of reversible color changes, controller 48 may be programmed to reverse or further alter the operational mode changes in image sensor 46 in the event that a condition tester ceases to detect the changed color of material 202.

The TLC can be used in several forms according to several embodiments, including but not limited to paints, microencapsulated coatings and slurries, TLC coated polyester sheets, and unsealed films.

As shown in FIG. 2, temperature-sensitive color-changing material 202 may be placed on the inside of capsule 200, with color-changing portions facing inwards. By placing material 202 on the inside of the capsule, potential problems associated with the biocompatibility and the resilience of material 202 in light of bodily fluids and pH changes may be avoided. However, it should be apparent that color-changing material may also be placed on the outside of capsule 200 where it may be in contact with bodily fluids. Such contact between material 202 and bodily fluids may facilitate testing of such bodily fluids for reactions with material 202. In certain embodiments, it may be necessary to achieve contact between bodily fluids and material 202. The attachment or placement of material 202 can be accomplished in several ways. For example, material 202 may be in the form of paint, and may be painted onto the capsule. In another embodiment, material 202 may be attached onto the capsule with adhesive. In a further embodiment, material 202 may be sprayed onto the dome 44 as a coating. In yet a further embodiment, material 202 may be enclosed in a semi-permeable membrane in contact with bodily fluids.

In the course of the function of capsule 200, light from a light source 204 may be directed towards material 202. Light source 204 may include one or several components, preferably light emitting diodes (LEDs) that may be placed in various locations within capsule 200. Light source 204 may also be used as or provided by illumination source 42 shown in FIG. 1, to illuminate the environment being imaged (outside of the capsule), or a separate illumination source 204 may be included for that purpose.

Changes in in vivo conditions, such as, for example, changes in temperature, pH, pressure, the presence of blood and the like (depending on the nature of material 202), may in certain embodiments cause various materials that can be used as color-changing material 202, to change color. Image sensor 46 detects the appearance of the new color when light from light source 204 is reflected back from material 202 onto image sensor 46. Referring to FIG. 2, such detection of changes in color may in certain embodiments be performed by a subgroup of pixels 206 included in the pixel array of image sensor 46. In one embodiment of the invention, pixel array of image sensor may have one subgroup of pixels that are sensitive to a first range of wavelengths e.g., colors and another subgroup of pixels sensitive to second range of wavelengths, e.g., colors. In some embodiments such one subgroup of pixels, or specific pixels may be positioned on the pixel array of image sensor 46 to be exposed to light reflected back from material 202 considering the angle of incidence 208 and angle or return 208' of the light directed onto and reflected back from material 202. Similarly, in certain embodiments, such subgroup of pixels 206 may be sensitive to a specified range of colors that appear on material 202 once the designated in vivo environmental condition may be detected. In an alternative embodiment special photodiode(s) may be used in addition to or in place of a subgroup of pixels 206 to detect color changes.

When a designated change in color of material 202 is detected by a subgroup of pixels 206, a signal may be sent to controller 48 by such a subgroup of pixels 206 or by another component operatively connected to a subgroup of pixels 206. In certain embodiments, a subgroup of pixels 206 may be replaced or supplemented by a spectral analyzer that is capable of detecting color changes in material 202. Other color-sensitive detectors may also be used. Such detection or processing may also be aided or performed by a processor or circuitry located in ASIC 50, external receiver 12 or data processor 14.

In certain embodiments, a range of color sensitive pixels, some of which may be sensitive to the various colors that can appear on material 202 may be situated on the pixel array of image sensor 46. Signals produced by each of such specific pixels 206 may vary depending on the color appearing on material 202. Controller 48 may detect and differentiate between such various signals, for example by utilizing appropriate image processing algorithms, and issue instructions to a sensor in response to each thereof. According to one embodiment a change of color may be detected in the in vivo environment that is being imaged. For example, a spot of bleeding may appear in a certain image. The change of color, that may indicate, for example, pathology in the GI tract, may be recognized by known methods. For example, controller 48 or data processor 14 may generate a probability indication of presence of colorimetric abnormalities on comparison of color content of the images and at least one reference value, for example, as described in PCT publication WO 02/073507, published on 19 Sep., 2002, that is assigned to the common assignee of the present invention. According to some embodiments, once a color change may be detected the controller 48 or data processor 14 may initiate a change in the mode of operation of device 40, of the external receiver 12, of both or of any other component or combination of components of the system. In other embodiments, a photodiode maybe used to detect changes in material 202. Such photodiode may in certain embodiments be connected to an amplifier that may be further connected to a comparator. A mode change may thereby be triggered by analog rather than digital electronics.

In one embodiment of the invention, one or more photodiodes may be used to detect light, such as for example, visible light, IR light, or other ranges of light illuminated for example externally through the skin toward an in vivo area of interest. A photodiode or other light detecting unit, for example incorporated in an in vivo device may sense illumination when approaching for example toward such area of interest. Such detection may trigger a change in operational mode. Other suitable signals besides light may be used to penetrate the skin or other tissue and other suitable detection units may be used to pick up penetrated signal in vivo. For example, an acoustic signal may be used.

In an embodiment, capsule 200 may operate in a low power consumption mode until a color change in material 202 may be detected. For example, until such color change may be detected, light sources 204 may be set to illuminate once every second, thereby consuming less power than used by the overall capsule 200 during full operation that might in certain embodiments illuminate several times a second or more. In response to a signal that may be detected from specific pixels 206, controller 48 (or another component located in capsule 200, external receiver 12 or data processor 14) may alter the mode of operation of capsule 200 or of any other component of the system. For example, in certain embodiments, any or both of light source 204 and image sensor 46 may be directed to increase the rate of capture of images in order to more fully image the endo-luminal vicinity wherein a specific condition may have been detected. Controller 48 may direct other activations or alterations in the mode or operation of capsule 200. In other embodiments, the response of controller 48 to signals from specific pixels 206, may be, for example, any of turning on the image sensor 46 that may theretofore have been inactive, changing mode of image sensor or transmitter, collecting samples of in vivo liquids or other materials, releasing encapsulated drugs that were held in capsule 200 or performing other functions.

In some embodiments, the pixels receiving the color indication may be, for example, the regular pixels of image sensor 46. Post processing circuitry or software located in capsule 200, external receiver 12 or data processor 14 may analyze the signals from the set of pixels (set being understood to include one unit) and make a mode change determination therefrom.

Other embodiments besides colorimetric changes may include, for example, temperature measurement using devices such as thermistors (located in a capsule for example as a discrete component or as part of ASIC) or using pH electrodes, and other embodiments.

Figure 3:
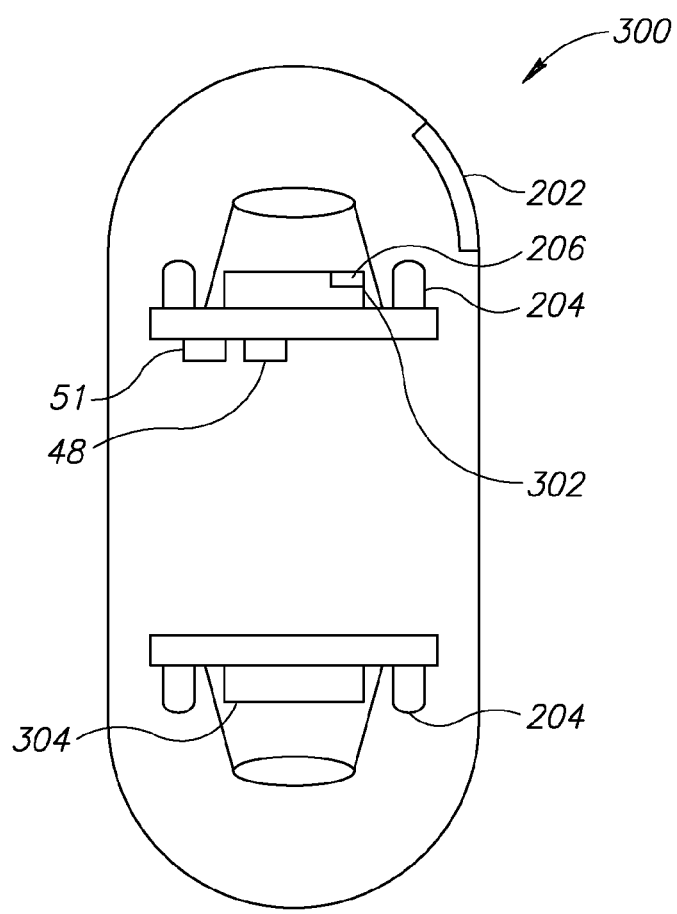
FIG. 3 is a schematic illustration of a device with two image sensors in accordance with an embodiment of the present invention.

Reference is now made to FIG. 3 that is a schematic illustration of a capsule 300 with two image sensors in accordance with an embodiment of the present invention. Capsule 300 has one image sensor 302 at one end of capsule 300 and a second image sensor 304 at another end of capsule 300. In an embodiment of the present invention, condition tester such as a color-changing material 202 such as those described in FIG. 2 may be installed proximate to image sensor 302, and such image sensor 302 may in such embodiment have specific pixels 206 similar to those described above for detecting color changes in material 202. When a change in color of material 202 is detected by image sensor 302, a signal of such change is sent to controller 48 of capsule 300. Controller 48 may in such embodiment alter the operational mode, such as for example by activating a component, for example the image sensor 304 of capsule 300. For example, the operational mode of both or either of image sensors 302 and 304 may be changed. Such a mode change may, for example, increase the number of images to be captured of such area or alter the orientation of images captured or differential activation of either one or both image sensors may be affected in response to a signal, or other mode changes discussed herein.

In certain embodiments, controller 48 may be configured to delay issuing operational mode change orders to until more than one signal from condition detector 49 may have been received. In an embodiment of the present invention, controller 48 may be configured with a delay mechanism in the form of for example a counter 51 that causes controller 48 to delay activating or altering the operational mode of image sensor 304 until several signals from condition tester 202 may have been received, or until signals signifying that a certain condition exists may be received over the course of a certain period of time. Such activation may, for example, reduce the chance that a false reading or fleeting condition activates image sensor 304, or may provide "debouncing" in case conditions may change in a variable manner between one relatively steady state and another. For example, in one embodiment, capsule 300 may operate in a first mode (e.g., low power consumption, or at a first frame capture rate) in the mouth and esophagus, where the pH is generally approximately 7-8. When capsule 300 reaches the stomach, where the pH is typically about 2, a pH detector on or within capsule 300 may detect a change in pH, and the operational mode may change, for example to a different power consumption, or a different frame capture rate. Later, when capsule 300 reaches the small intestine, capsule 300 may detect a change in pH to, for example 7-8, and the operational mode may change again. A change in pH may cause alteration in the operational mode only if received for, for example, one minute (other suitable time periods may be used). Other methods of debouncing or guarding against fleeting conditions may be used.

Figure 8:
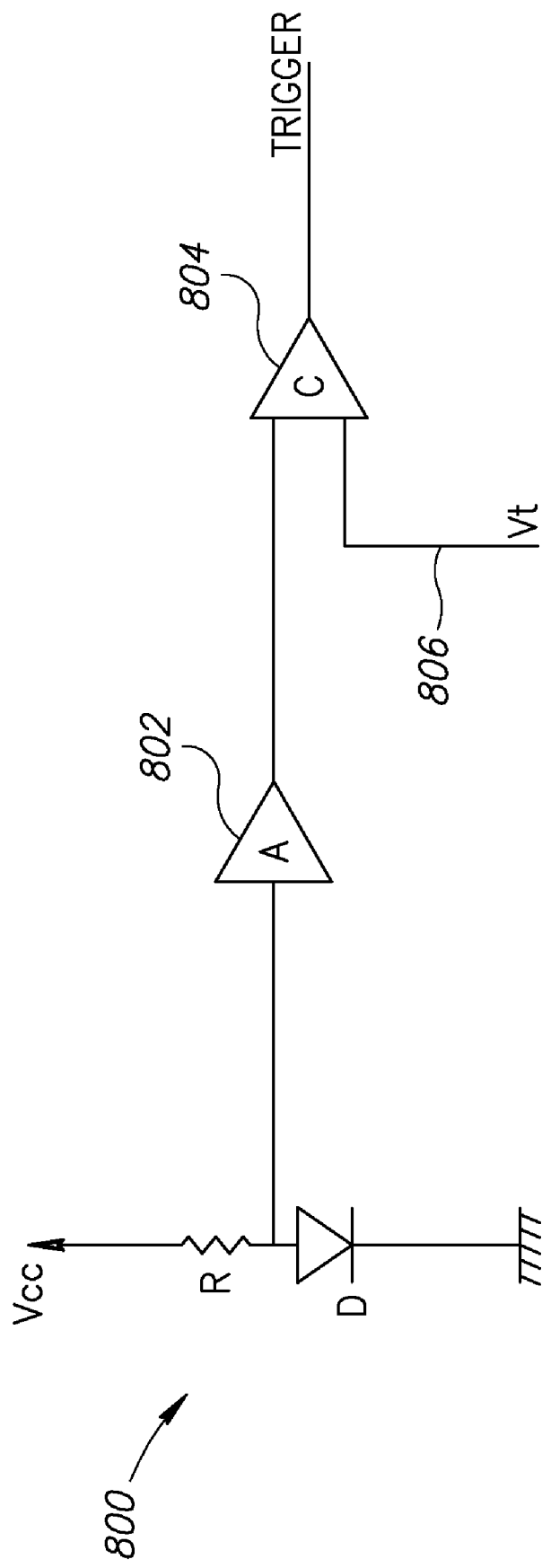
FIG. 8 sets forth a schematic diagram of a temperature triggered circuit in accordance with an embodiment of the current invention.

Controller 48 may in certain embodiments be a software controller embedded into ASIC 50. In other embodiments, controller 48 may be a simple switch or circuit connected to for example a condition tester such as a thermistor 800. The controller may include, for example, an amplifier 802 and a comparator 804, comparing the measured signal to some pre-defined threshold 806, as are depicted forth, for example, in FIG. 8. Such switch or circuit may in certain embodiments power on or trigger the activation of ASIC 50 when the proper condition may be detected. In other embodiments, such switch or circuit may signal ASIC 50 to, for example, begin operation or change the mode of operation of the sensor.

Figure 4:
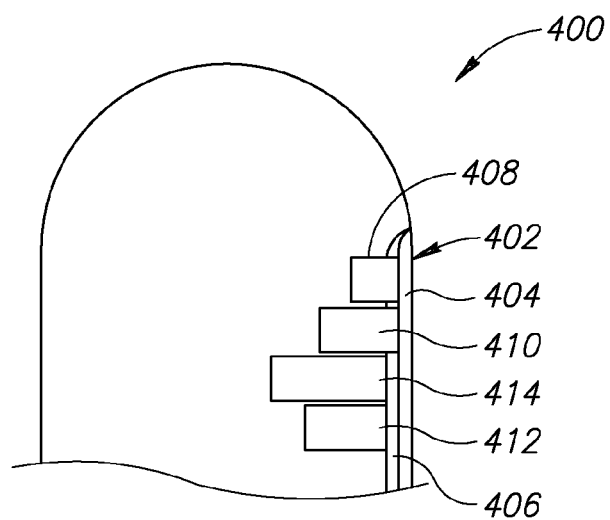
FIG. 4 is a schematic illustration of a condition tester in the form of a coating in accordance with an embodiment of the present invention.

In a further embodiment, the switch from one condition and then back to another may be the trigger for a mode change. For example, in case a high pH is detected for a period, then a low pH, then again a high pH, the mode change may occur only on the third condition change. Other suitable signals or series of signals may be used to trigger other suitable functionalities. Further, altering the mode based on detection of a condition change may be combined with, for example, a delay. For example, capsule 300 may wait, for example, one hour after detecting a condition change to effect a mode change. FIG. 4 is a schematic illustration of a condition tester in the form of a coating in accordance with an embodiment of the present invention. In such embodiment, a portion of capsule 400 may be coated with one or more layers of a dissolvable material 402. Each layer of dissolvable material 402 may be comprised of varying substances that dissolve at varying rates or when exposed to specific materials or environments. For example, a first, outer layer 404 of dissolvable material may be pH sensitive and dissolve when exposed to the acidic environment of the stomach, and may expose certain components such as for example switches 412, sensors 408 or drug compartment 410 with an opening, while capsule 400 may be in a specified site such as for example, the stomach. A second inner layer 406 may for example, dissolve in the more basic environment of the small intestine and may activate other sensors or release other encapsulated drugs. Other materials that may be sensitive to elapsed time and dissolve in accordance with a specific period of time after introduction to the GI tract may also be possible as a means of delaying activation of certain functions of capsule 400. An example of dissolvable materials that may be used as such coatings include starches, such as gelatinous materials, waxes, biodegradable plastics, and other known biodegradable materials. Other suitable dissolvable materials with other characteristics may also be used.

Dissolvable material 402 may cover any or all of a sensor 408, such as for example, a pH sensor, a switch 412, such as for example a switch that turns on an image sensor, an encapsulated drug compartment 410 that releases its contents or a sampling inlet 414 that lets surrounding fluids enter a compartment where such fluids may be sampled, captured or evaluated by a sensor. When dissolvable material 402 dissolves, sensor 408 may be exposed, switch 412 may be activated, sampling inlet 414 may be opened or an encapsulated drug compartment 410 may release its contents into the surrounding area. In other embodiments, the dissolving of dissolvable material 402 may facilitate contact between electrical leads that had theretofore been separated, such contact may signal a change in operational mode. According to another embodiment a magnet may be held in the vicinity of the capsule 400 such that it affects the ON/OFF status of the capsule. In some embodiments the magnet may be embedded in a dissolvable coating, such as dissolvable material 402, such that while the coating is intact, the capsule is OFF. When the coating dissolves, for example, in response to environmental pH, the magnet may be freed and may become dissociated from the capsule allowing the capsule to be ON. In other embodiments other suitable environmental triggers may cause the dissolving of coatings.

Figure 5A:
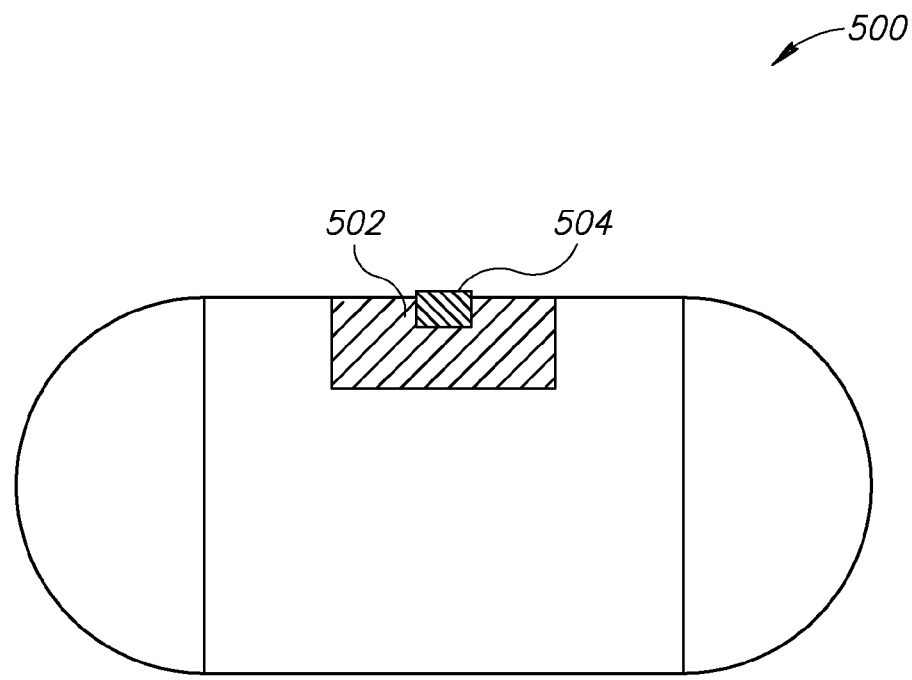
FIGS. 5A and 5B are schematic illustrations of a floatable device according to an embodiment of the invention.
Figure 5B:
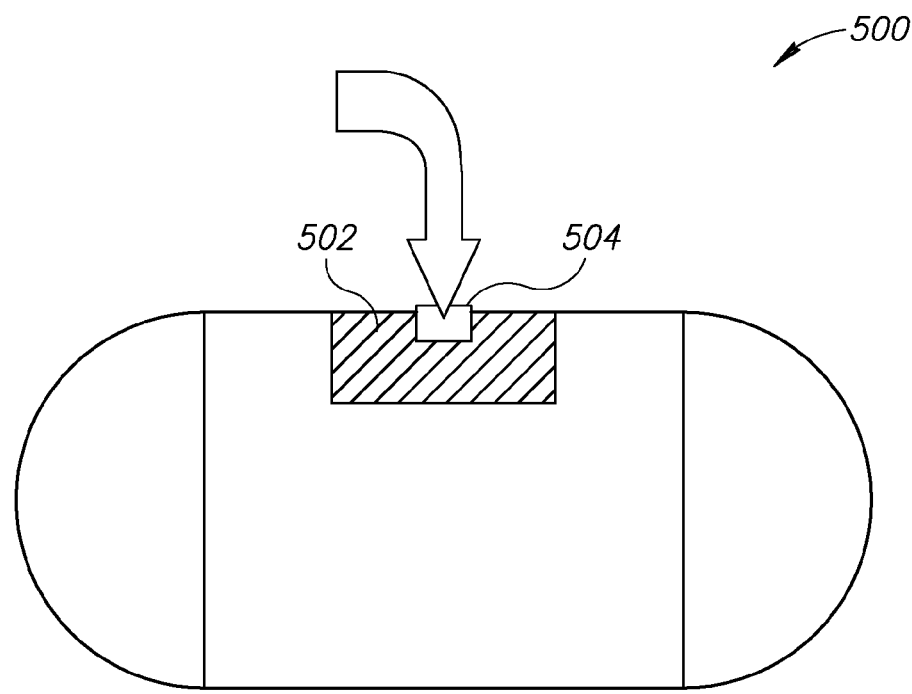

Another embodiment is schematically illustrated in FIGS. 5A and 5B. In this embodiment an imaging capsule 500 may be a floatable capsule, for example, a capsule having a specific gravity of less than 1. A floatable capsule is described, for example, in Publication Number WO 02/095351, published on Nov. 28, 2002 assigned to the common assignee of the present inventions and is hereby incorporated in its entirety by reference. Such a capsule may be advantageous for passage through portions of a voluminous cavity, such as the stomach and/or large intestine. In other portions of voluminous cavities (e.g., the descending portion of the large intestine) a floatable capsule may be delayed rather than advanced. Thus, a floatable capsule may benefit from having the option of loosing its floatation characteristics at a given point during its passage through the GI tract, for example, while in the large intestine.

According to one embodiment, a capsule may have a fluid chamber such as for example a floatation compartment 502 that may be filled with a fluid, a gas, or other suitable material that is lighter than the endo-luminal fluid, for example, air. In certain embodiments, floatation compartment may be as small as 5% of the volume of capsule 500. Other suitable volumes may be used. The floatation compartment 502 may have a valve 504 keeping the compartment 502 closed and the capsule 500 floating. Upon triggering, valve 504 may be opened (see FIG. 5B). Floatation compartment 502 may then be filled with endo-luminal liquid, raising the specific gravity of capsule 500 and rendering capsule 500 non-floating. As such the floatation mode of a capsule may be altered.

A number of mechanisms for opening valve 504 may be implemented, such as, electronic, mechanical or chemically based mechanisms. For example instant heating (requiring only a small amount of battery energy) may be applied, melting material of valve 504. The signal for effecting the change may be as described above.

Figure 6:
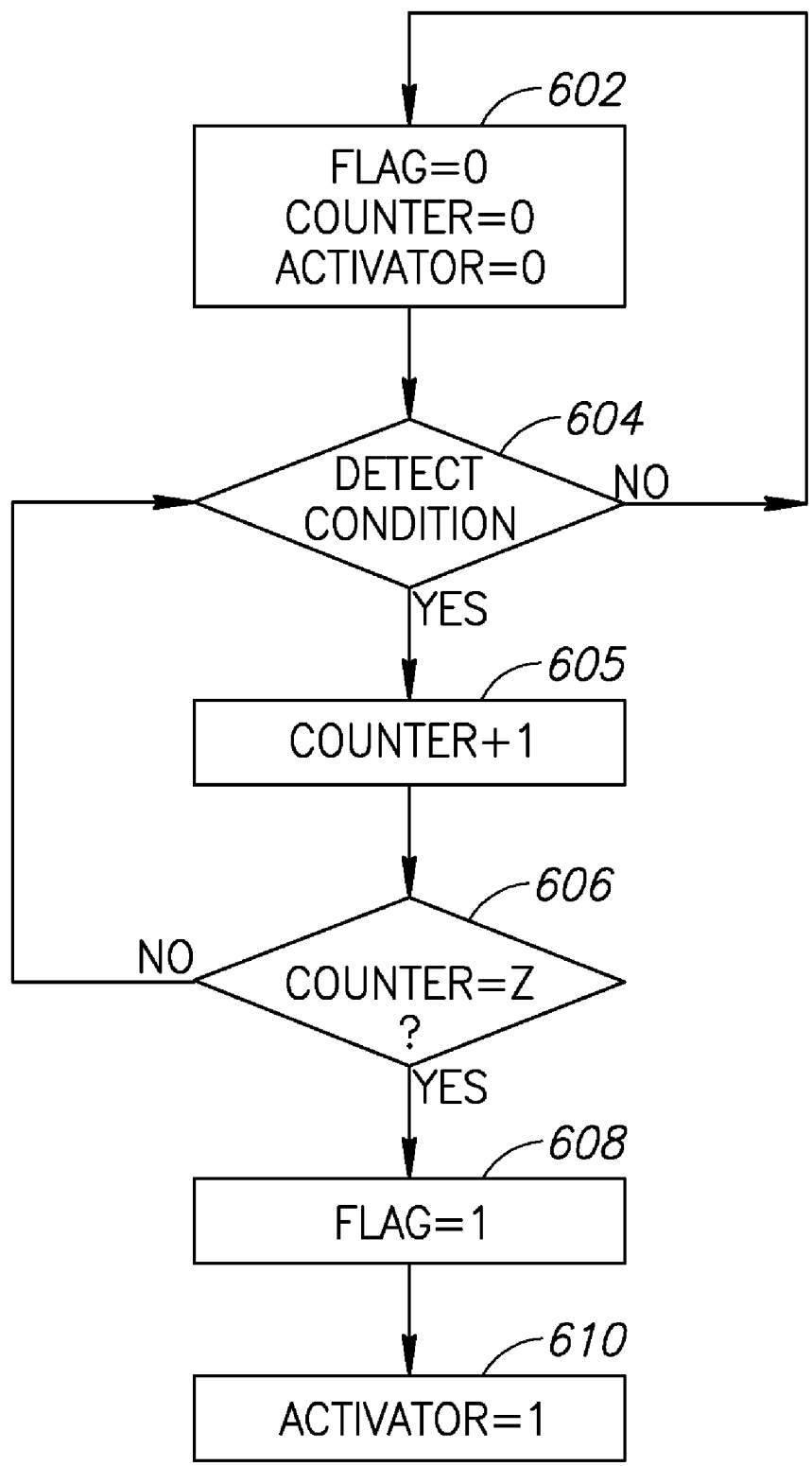
FIG. 6 sets forth a flow chart of the operation of a controller in accordance with an embodiment of the present invention.

FIG. 6 sets forth a flow chart of the operation of a controller 48 in accordance with an embodiment of the present invention. Such controller may in an embodiment be a software controller in the form of logic programmed into, for example ASIC 50, controller 48, external receiver 12 or other suitable components. Such software controller may have a flag to indicate the operational mode to which a sensor is set. Settings of such flag may be 0 or 1 for on or off, or other suitable settings to indicate other settings to which a sensor may then be operating. Software controller may also include a counter that may in certain embodiments count signals received from condition tester 49 indicating the detection of the conditions to be tested by condition tester 49. Software controller may also be operatively linked to an operation activator of an in vivo component such as image sensor 46 that controls the operation of such sensor. For example, operation activator may be an internal clock that controls the timing of the image capture rate of image sensor 46 or the operation of light source 204.

In its initial state 602, the flag of software controller may be set to 0, the counter may be set to 0 and the activator may be set to 0. In such settings, image sensor 46 may not be capturing images or may be in some other reduced mode of operation. In step 604, condition tester 49 may detect a changed condition in the in vivo area surrounding capsule 40 and may signal software controller 48 as to such changed condition. Such signal increments counter to 1 Step 604 may be repeated by condition tester 49 at periodic intervals that match the sampling rate of condition tester 49. Each signal delivered by condition tester 49 that indicates the changed condition may increment the counter by 1 (605). Once the counter reaches a designated threshold in step 606, the flag switches to 1 in step 608. Such switch by the flag to 1 switches the sensor activator to 1 as in Step 610. The activator may then change the mode of operation of image sensor 46. Such change may for example be an increase in the frame capture rate of image sensor 46 or any other suitable change in the operational mode of the sensor.

In certain embodiments, the counter may be decremented each time condition tester 49 sends a signal to controller 48 that indicates the absence of an elevated condition, thereby possibly indicating that conditions may have returned to pre-defined normal levels. Once the counter may have been decremented below a pre-defined threshold level, the flag may revert to 0 and may reset the activator to its initial setting so that such sensor may resume the operational mode that was in effect prior to the change described above, or some other suitable operational mode.

In other embodiments, condition tester 49 may be, for example, a clock such as for example an internal clock embedded into ASIC 50 or otherwise operatively connected to image sensor 46. In such case, controller 48 may be a component such as for example a switch operatively attached to such embedded clock that may turn on once a designated period has elapsed. Such elapsed period may be the estimated time that it takes capsule 300 to pass through the stomach and into the small intestine where the desired image capturing may take place. Other periods may also be designated depending on where in the GI tract the desired image capturing may be designated to begin.

Figure 7:
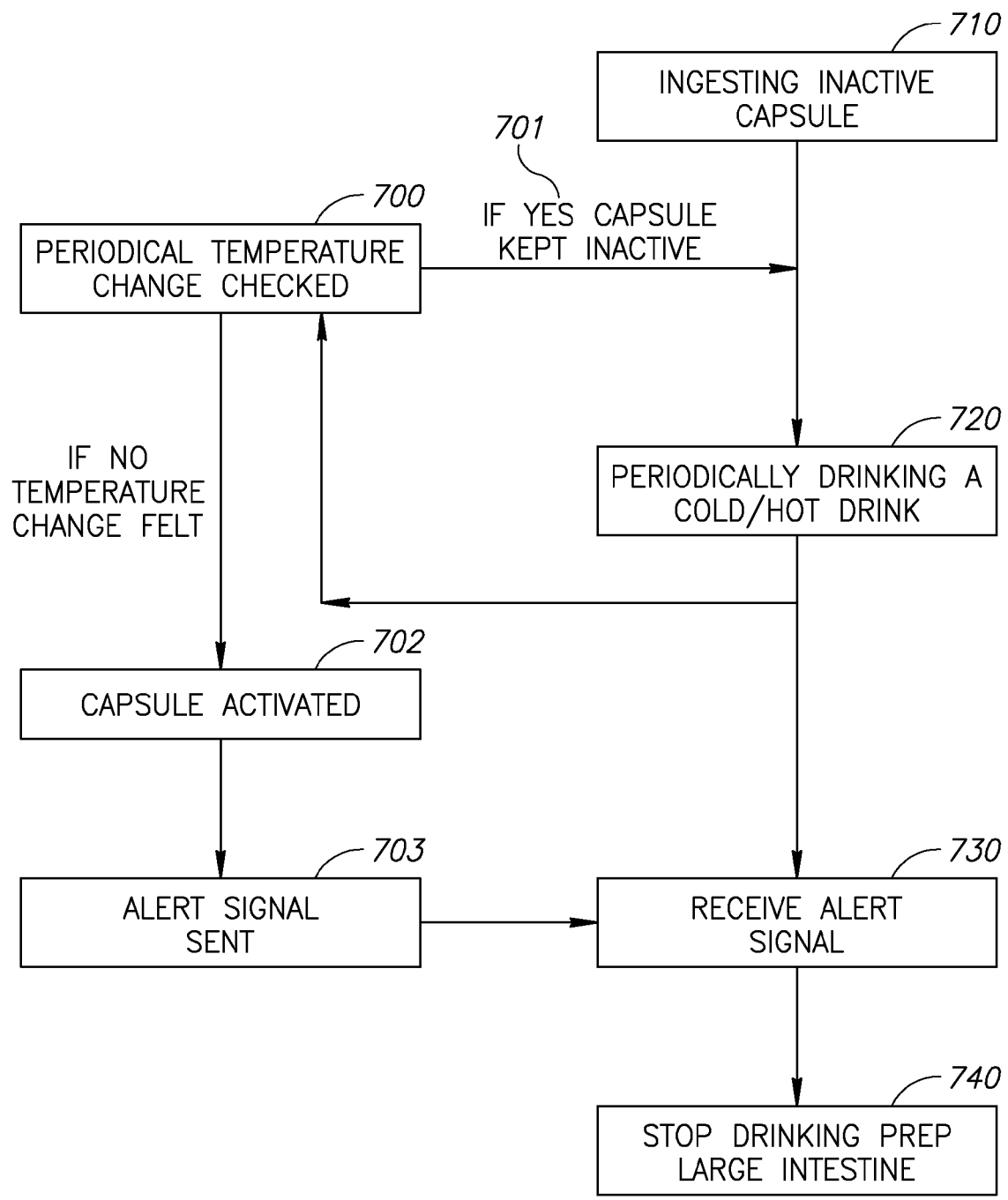
FIG. 7 sets forth a flow chart of the operation of a device in accordance with an embodiment of the present invention.

In yet further embodiments, an ingestible capsule may be meant for imaging or otherwise sensing distal portions of the GI tract, such as the large intestine. A method for economically using an imaging (or other sensing) capsule is provided according to an embodiment of the invention. FIG. 7 illustrates a method for imaging or otherwise sensing distal parts of the GI tract according to an embodiment of the invention. An inactive device such as for example a capsule (e.g., does not sample or transmit images or other data) is swallowed (710) by a patient. According to one embodiment the capsule may comprise temperature sensing capabilities. Any in vivo temperature sensing mechanism, such as those known in the art, may be used. After a capsule is swallowed a patient may be made to ingest a volume of cold or hot water (720) at regular intervals. According to one embodiment the patient may ingest cold or hot water over a period of a few hours (e.g., 3-5 hours), for example, a period in which the capsule has most probably left the stomach. According to another embodiment the patient may be made to ingest a volume of cold or hot water until alerted that the capsule has left the stomach (further detailed below). While the capsule may be in the stomach an ingested volume of cold or hot water may cause a change of temperature in the stomach environment. Once in the small intestine, the effect of a cold or hot drink may no longer be felt. According to one embodiment a capsule may be programmed to sense a periodical change in temperature (700), for example to sense a temperature above or below a certain threshold, at predetermined intervals. While a temperature change may be sensed at predetermined intervals, the capsule may be kept inactive (701). If a temperature change is not sensed at one predetermined time, the capsule may be triggered (for example, as detailed above) to activate the image sensor or other components (702). Thus, the capsule may begin collecting data only after leaving the stomach for example, such that it is closer to the large intestine thereby saving energy and allowing effective and complete action of the capsule in the large intestine.

According to some embodiments activating the capsule may cause a signal to be transmitted (703) to an external receiving unit so as to activate an alert 730 (e.g., a beep or a flashing light), that may alert a patient to start or stop an action for example to stop drinking the cold or hot drink (740). Also, the patient may then be prepared for the expected imaging or otherwise sensing of the large intestine, for example, the patient may thus be warned to begin taking a laxative.

Figure 9:
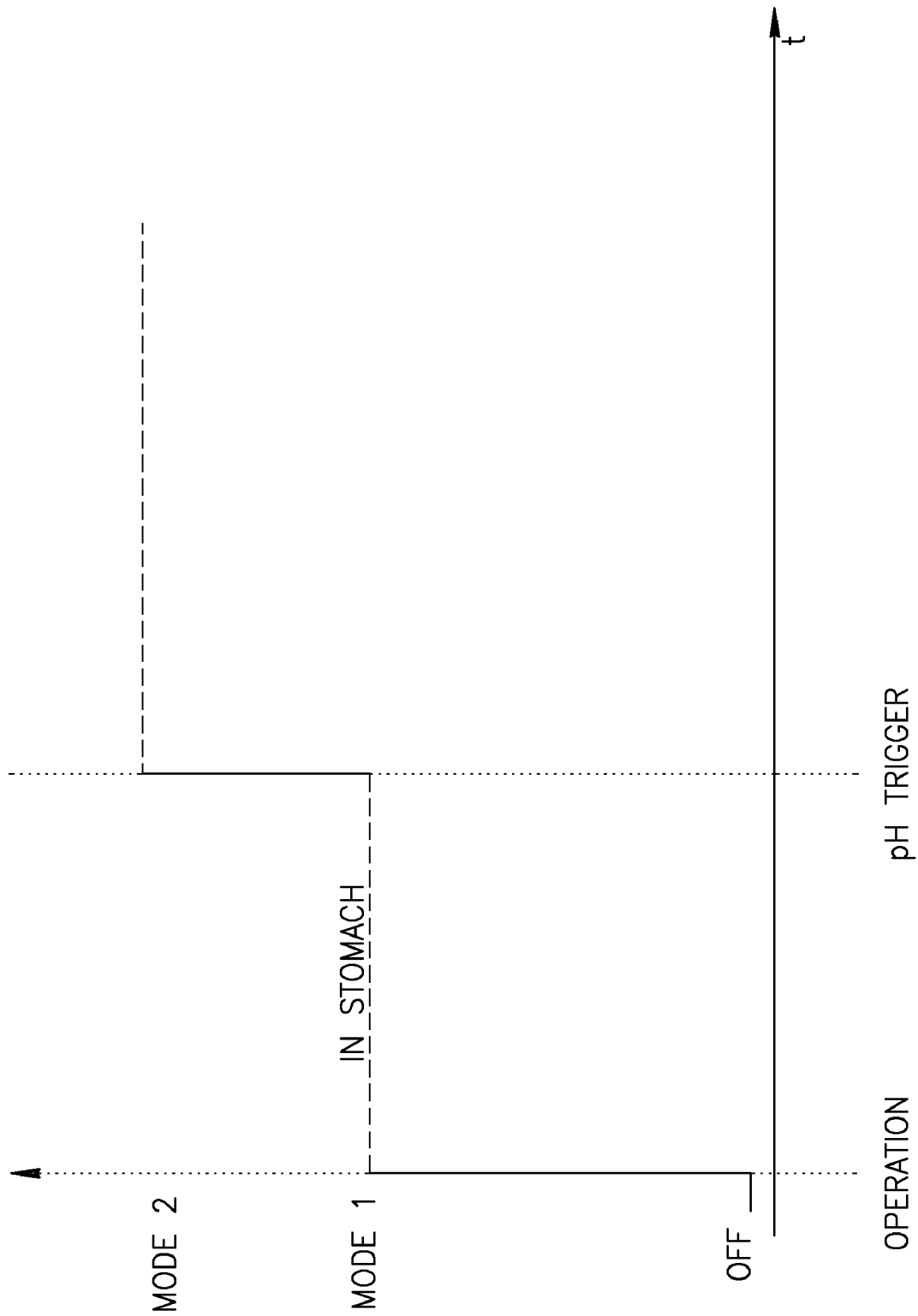
FIG. 9 is a chart depicting a change in mode based on a pH trigger in accordance with an embodiment of the current invention.

Reference is made to FIG. 9 that is a chart depicting a change in mode based on a pH trigger in accordance with an embodiment of the current invention. As depicted in FIG. 9, a device may be in a first operational mode from, for example beginning with the time it is turned on and while it is for example, in the stomach wherein pH is low. As the device may leave the stomach, pH may rise. Such rise may set off the pH trigger that may change the operational mode of the device. Other suitable triggers may be used as well. Such change may, for example, be a component such as for example a switch of the device imaging with two image sensors 302 and 304 (as are depicted, for example, in FIG. 3) to imaging with only a first image sensor 302. In such an embodiment effective viewing of the upper regions of the GI tract may be enabled, by using two image sensors whereas, a power saving mode may then be switched to in the small intestine where one image sensor may be enough to provide effective viewing.

Figure 10:
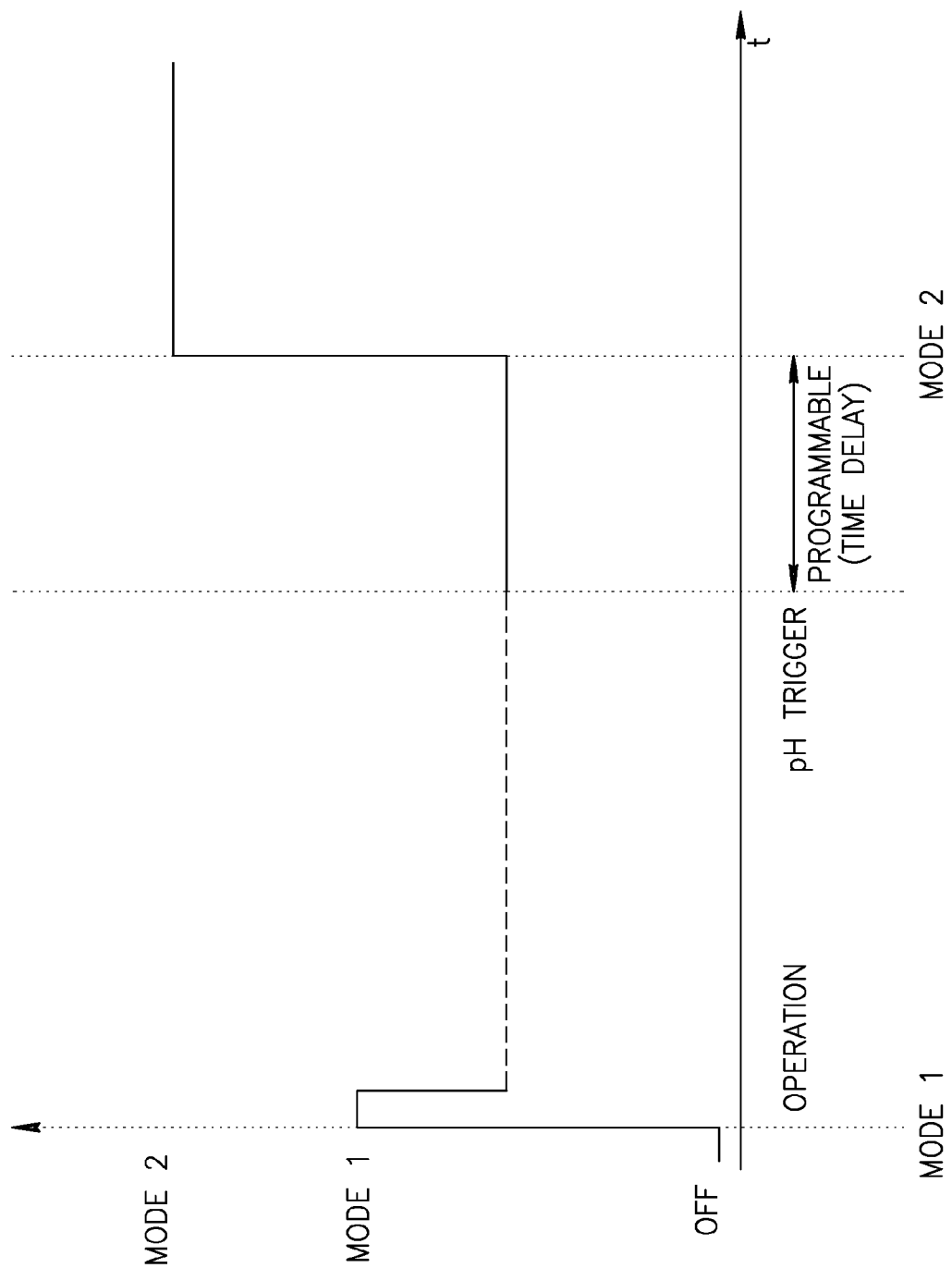
FIG. 10 is a chart depicting a change in mode initiated by a pH trigger and combined with a timed delay in accordance with an embodiment of the current invention.

Reference is made to FIG. 10 that is a chart depicting a change in mode initiated by a pH trigger and combined with a timed delay in accordance with an embodiment of the current invention. As depicted in FIG. 10, a device may be in a first mode of operation immediately when it is introduced into a body. The mode of operation may change, such as for example, going to off or some other inactive state, until a trigger occurs such as for example a change in pH. Other suitable triggers may be used as well. The trigger may initiate, for example, a time delay during which the mode of operation may remain initially unchanged, but during which the device counts down until the delay ends, whereupon the mode change may be implemented. A trigger combined with a time delay may be useful for example where the large intestine may be the area to be imaged. In such an embodiment, the trigger may be the pH change that occurs when the device leaves the stomach. The time delay may be the approximate time required for the device to traverse the small intestine (e.g., 3-6 hours). Once the device nears the large intestine it may change modes of operation to image the desired area. In this way, the device may preserve its power supply until many hours after it is introduced into a body and until it reaches the targeted imaging area. Other suitable combinations of time delays and triggers are possible.

It will be appreciated by persons skilled in the art that the present invention is not limited by what has been particularly shown and described herein above. Rather the scope of the invention is defined by the claims.

We claim:

1. A system for in-vivo sensing at a specified site along the GI tract, the system comprising:

an autonomous in-vivo capsule comprising:
- a condition tester configured to test an in-vivo condition, the condition tester comprising at least one layer of dissolvable material coated on at least a portion of the capsule, wherein the at least one layer dissolves when exposed to a specified material of a specified site along the GI tract; and
- a component selected from the group consisting of: a sensor which is exposed when the layer dissolves and a switch which is activated when the layer dissolves;
- wherein said capsule further comprises a controller configured to delay issuing operational mode change orders until more than one electrical signal from said condition tester has been received.

2. The system according to claim 1, wherein the at least one layer comprises pH sensitive dissolvable material.

3. The system according to claim 1, comprising a second sensor and a second layer of dissolvable material, wherein the at least one layer of dissolvable material coats the first sensor, and the second layer of dissolvable material coats the second sensor.

4. The system according to claim 3, wherein the first layer dissolves when exposed to a different material than the material in response to which the second layer dissolves.

5. The system according to claim 3, wherein the first layer dissolves at a different specified site along the GI tract than the specified site at which the second layer dissolves.

6. The system according to claim 3, wherein the first and second layers comprise different substances that dissolve at different rates.

7. The system according to claim 1, comprising an image sensor, wherein said component is a switch, and the switch turns on the image sensor.

8. The system according to claim 1, wherein the system comprises at least one component selected from the group consisting of an encapsulated drug compartment and a sampling inlet, the component covered by the at least one layer of dissolvable material.

9. A method for in-vivo sensing at a specified site along the GI tract, the method comprising:
- testing an in-vivo condition using a condition tester, the condition tester comprising at least one layer of dissolvable material coated on at least a portion of a capsule;
- dissolving the at least one layer by exposing the layer to a specific material of a specified site along the GI tract;
- exposing a sensor when the layer dissolves; and
- delaying the issuance of operational mode change orders until more than one electrical signal from said condition tester has been received.

10. The method according to claim 9, wherein dissolving the at least one layer comprises exposing the layer to an environment with a specific pH.

11. The method according to claim 9, comprising coating the first sensor with the at least one layer of dissolvable material and coating a second sensor with a second layer of dissolvable material.

12. The method according to claim 11, wherein the first layer dissolves when exposed to a different material than the material in response to which the second layer dissolves.

13. The method according to claim 11, wherein the first layer dissolves when exposed to a different specified site along the GI tract than the specified site at which the second layer dissolves.

14. The method according to claim 11, wherein the first layer dissolves at a different rate than the rate at which the second layer dissolves.

15. A method for in-vivo sensing at a specified site along the GI tract, the method comprising:
- testing an in-vivo condition using a condition tester, the condition tester comprising at least on layer of a dissolvable material coated on at least a portion of a capsule;
- dissolving the at least one layer by exposing the layer to a specific material of a specified site along the GI tract;
- exposing a switch which is activated when the layer dissolves; and
- delaying the issuance of operational mode change orders until more than one electrical signal from said condition tester has been received.

16. The method according to claim 15, wherein dissolving the at least one layer comprises exposing the layer to an environment with a specific pH.

17. The method according to claim 15, comprising coating a first sensor with the at least one layer of dissolvable material and coating a second sensor with a second layer of dissolvable material.

18. The method according to claim 17, wherein the first layer dissolves when exposed to a different material than the material in response to which the second layer dissolves.

19. The method according the claim 17, wherein the first layer dissolves when exposed to a different specified site along the GI tract than the specified site at which the second layer dissolves.

20. The method according to claim 17, wherein the first layer dissolves at a different rate than the rate at which the second layer dissolves.

* * * * *

UNITED STATES PATENT AND TRADEMARK OFFICE
CERTIFICATE OF CORRECTION

| | | |
|---|---|---|
| PATENT NO. | : 8,216,130 B2 | Page 1 of 1 |
| APPLICATION NO. | : 12/854483 | |
| DATED | : July 10, 2012 | |
| INVENTOR(S) | : Arkady Glukhovsky | |

It is certified that error appears in the above-identified patent and that said Letters Patent is hereby corrected as shown below:

On the cover page, item (75), replace the second inventor's name "Mordechsi Frisch" with --Mordechai Frisch--

Signed and Sealed this
Twenty-fifth Day of September, 2012

David J. Kappos
*Director of the United States Patent and Trademark Office*